United States Patent
Usuda et al.

(10) Patent No.: US 10,462,342 B2
(45) Date of Patent: Oct. 29, 2019

(54) IMAGING MODULE AND IMAGING-MODULE-ATTACHED CATHETER

(71) Applicant: FUJIKURA LTD., Tokyo (JP)

(72) Inventors: Hideaki Usuda, Tokyo (JP); Kenichi Ishibashi, Sakura (JP); Daisuke Murakami, Sakura (JP); Takeshi Ishizuka, Sakura (JP); Yoshinobu Numasawa, Sakura (JP); Shingo Ishii, Tokyo (JP)

(73) Assignee: FUJIKURA LTD., Tokyo (JP)

( * ) Notice: Subject to any disclaimer, the term of this patent is extended or adjusted under 35 U.S.C. 154(b) by 0 days.

(21) Appl. No.: 16/115,217

(22) Filed: Aug. 28, 2018

(65) Prior Publication Data
US 2019/0068858 A1  Feb. 28, 2019

(30) Foreign Application Priority Data

Aug. 31, 2017 (JP) .................. 2017-167993

(51) Int. Cl.
| A61B 1/04 | (2006.01) |
| H04N 5/225 | (2006.01) |
| A61B 1/00 | (2006.01) |
| A61B 1/05 | (2006.01) |
| G02B 23/24 | (2006.01) |

(52) U.S. Cl.
CPC ....... H04N 5/2257 (2013.01); A61B 1/00114 (2013.01); A61B 1/04 (2013.01); A61B 1/05 (2013.01); G02B 23/2476 (2013.01); H04N 5/2253 (2013.01); H04N 2005/2255 (2013.01)

(58) Field of Classification Search
CPC ............... H04N 5/2257; H04N 5/2253; H04N 2005/2255; G02B 23/2476; A61B 1/04; A61B 1/05; A61B 1/00114
See application file for complete search history.

(56) References Cited

U.S. PATENT DOCUMENTS

| 5,873,816 A | 2/1999 | Kagawa et al. |
| 6,086,528 A | 7/2000 | Adair |
| 2006/0025651 A1 | 2/2006 | Adler et al. |

(Continued)

FOREIGN PATENT DOCUMENTS

| JP | H07-100101 A | 4/1995 |
| JP | H10-099267 A | 4/1998 |

(Continued)

OTHER PUBLICATIONS

Extended European Search Report issued in corresponding European Patent Application No. 18190482.2, dated Jan. 2, 2019 (8 pages).

*Primary Examiner* — Howard D Brown, Jr.
(74) *Attorney, Agent, or Firm* — Osha Liang LLP (57) ABSTRACT

An imaging module includes: an image-sensing device; a first substrate including a first insulating substrate main body; a second substrate including a second insulating substrate main body; and a signal cable disposed between the first substrate and the second substrate, that electrically connects a first cable terminal to a second cable terminal. In the imaging module, D1 is a length of a first diagonal line on a light-receiving face of the image-sensing device, D2 is a length of a second diagonal line on an end face of the second insulating substrate main body, and D2 is less than or equal to D1.

9 Claims, 8 Drawing Sheets

(56) References Cited

U.S. PATENT DOCUMENTS

| | | |
|---|---|---|
| 2008/0214892 A1 | 9/2008 | Irion et al. |
| 2014/0361153 A1* | 12/2014 | Motohara ............ G02B 6/4253 |
| | | 250/227.11 |
| 2015/0378144 A1 | 12/2015 | Handte et al. |
| 2016/0296102 A1* | 10/2016 | Shimono ............ A61B 1/00114 |
| 2018/0070799 A1* | 3/2018 | Sekido ..................... A61B 1/04 |

FOREIGN PATENT DOCUMENTS

| | | |
|---|---|---|
| JP | 2006-109097 A | 4/2006 |
| JP | 2012-139308 A | 7/2012 |
| JP | 2017-140426 A | 8/2017 |
| WO | 2016/194074 A1 | 12/2016 |

\* cited by examiner

IMAGING MODULE AND IMAGING-MODULE-ATTACHED CATHETER

CROSS REFERENCE TO RELATED APPLICATIONS

This application claims priority from Japanese Patent Application No. 2017-167993 filed on Aug. 31, 2017, the contents of which are incorporated herein by reference in their entirety.

BACKGROUND

Field of the Invention

The present invention relates to an imaging module and an imaging-module-attached catheter.

Description of the Related Art

An imaging module having a configuration in which a solid-state image sensing device (hereinbelow, may be simply referred to as an image-sensing device) is electrically connected to an end of an electrical cable with a wiring substrate interposed therebetween is often employed in electronic endoscopes (for example, Japanese Unexamined Patent Application, First Publication No. 2006-109097).

In this kind of imaging module, a plurality of ends of the electrical cable are electrically connected to wiring of the wiring substrate, and each electrical cable is electrically connected to the image-sensing device via the wiring of the wiring substrate.

In an imaging device such as an endoscope using the aforementioned imaging module, a configuration is often employed in which a plurality of electrical cables connected to an imaging module and a wiring substrate of the imaging module are accommodated in a tube. Furthermore, an back end that is opposite to the imaging module side of the electrical cable of this imaging device is drawn from the tube and is electrically connected to an image information processing device that receives imaging signals from the electrical cable and displays an image on a display device such as a monitor.

In recent years, it has been studied that an imaging module is applied to a medical instrument such as a catheter that is provided with a lumen or a working channel. For example, in the case of inserting an imaging module into a medical tube having a hole into which an image-sensing device is to be incorporated, it is necessary to draw the imaging module into the tube through the hole. However, in the case where a substrate size of the imaging module is larger, it is difficult to smoothly insert the imaging module into the hole formed in the tube.

SUMMARY

One or more embodiments of the invention provide an imaging module that can be easily drawn into a medical instrument that is provided with a channel such as lumen and has a small diameter.

An imaging module according to one or more embodiments of the invention includes: an image-sensing device including an image-sensing device electrode; a first substrate including a first substrate main body serving as an insulating member, a first wiring formed on the first substrate main body, an electrode terminal electrically connected to the image-sensing device electrode and the first wiring, and a first cable terminal that is formed on a surface of the first substrate main body and is electrically connected to the first wiring; one second substrate including a second substrate main body serving as an insulating member, a second wiring formed on the second substrate main body, and a second cable terminal that is formed on a surface of the second substrate main body and is electrically connected to the second wiring; and a signal cable that is provided between the first substrate and the second substrate and electrically connects the first cable terminal to the second cable terminal, wherein where a length of a first diagonal line on a light-receiving face of the image-sensing device is defined as D1 and a length of a second diagonal line on an end face of the second substrate main body is defined as D2, the length D2 is less than or equal to the length D1.

In the imaging module according to one or more embodiments of the invention, the signal cable may be arranged inside a circumscribed circle of the second substrate main body, and the circumscribed circle having a diameter corresponding to the length of the second diagonal line.

In the imaging module according to one or more embodiments of the invention, the image-sensing device may have an electrode surface on which the image-sensing device electrode is provided, and the first substrate may be connected to the electrode surface so that an end face of the first substrate main body is located between two image-sensing device electrodes.

In the imaging module according to one or more embodiments of the invention, the second substrate may have a first surface, a second surface opposite to the first surface, and a through electrode that penetrates through the second substrate main body between the first surface and the second surface, and the second wiring may be formed on the first surface and on the second surface and may be electrically connected to the through electrode.

In the imaging module according to one or more embodiments of the invention, the second substrate may include an external connection terminal formed on the second substrate main body, and the external connection terminal may be electrically connected to the second wiring.

In the imaging module according to one or more embodiments of the invention, the external connection terminal may be formed on the first surface of the second substrate.

In the imaging module according to one or more embodiments of the invention, the external connection terminal may be formed on the second surface of the second substrate.

In the imaging module according to one or more embodiments of the invention, the signal cable may be a coaxial cable.

An imaging-module-attached catheter according to one or more embodiments of the invention includes: the imaging module according to one or more embodiments; and a tube including: a module arrangement region in which the first substrate and part of the signal cable are arranged; and a channel that is located between the first cable terminal and the second cable terminal and is next to the module arrangement region, wherein as seen from the image-sensing device, the channel is disposed within an outline of the image-sensing device on a plane of projection.

As described above, according to one or more embodiments of the invention, it is possible to provide an imaging module that can be easily drawn into a medical instrument that is provided with a channel such as lumen and has a small diameter. Additionally, it is possible to provide a catheter including both a channel and an imaging module and having small-diameter.

DETAILED DESCRIPTION

Hereinafter, embodiments of the invention will be described with reference to drawings.

In the drawings showing embodiments of the invention, in order for the respective components to be of understandable size in the drawings, the dimensions and the proportions of the components are modified as needed compared with the real components.

Figure 1:
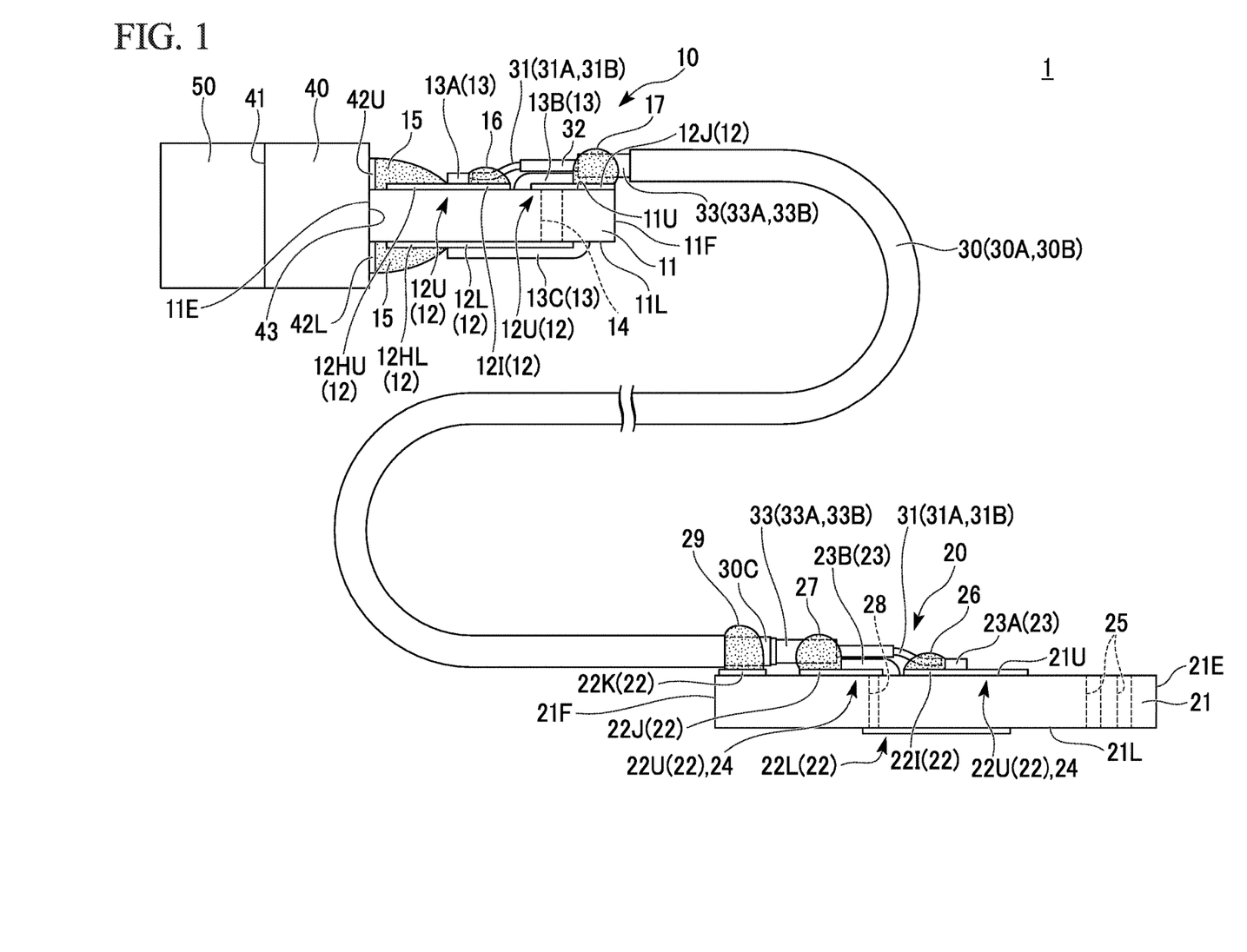
FIG. 1 is a partial cross-sectional view showing a schematic configuration of an imaging module according to one or more embodiments of the invention.

FIG. 1 is a partial cross-sectional view showing a schematic configuration of the imaging module 1 according to one or more embodiments of the invention.

The imaging module 1 includes a first substrate 10, a second substrate 20, a signal cable 30, a solid-state image sensing device 40 (image-sensing device), and a lens housing 50.

(First Substrate 10)

The first substrate 10 includes a first substrate main body 11 serving as an insulating member and a first wiring 12 (upper face wiring 12U, and lower face wiring 12L) formed on the first substrate main body 11. The first substrate main body 11 has an upper face 11U (first surface) and a lower face 11L (second surface) opposite to the upper face 11U. The upper face wiring 12U is formed on the upper face 11U. The lower face wiring 12L is formed on the lower face 11L. The first wiring 12 has a conductive wiring pattern formed on both the upper face 11U and the lower face 11L.

The first substrate main body 11 (first substrate 10) has an outer end face 11E (end face) connected to the solid-state image sensing device 40 and an inner end face 11F opposite to the outer end face 11E. In a state where the outer end face 11E is connected to the solid-state image sensing device 40, the first substrate main body 11 extends in a direction substantially orthogonal to an electrode surface 43 of the solid-state image sensing device 40. The inner end face 11F is exposed to a space adjacent to the signal cable 30.

The first substrate 10 includes a through electrode 14 that penetrates through the first substrate main body 11 between the upper face 11U and the lower face 11L. The through electrode 14 electrically connects the upper face wiring 12U to the lower face wiring 12L.

An electrode terminal 12HU that is electrically connected to the upper face wiring 12U is formed on the upper face 11U. An electrode terminal 12HL that is electrically connected to the lower face wiring 12L is formed on the lower face 11L. That is, electrode terminals are formed on both the upper face 11U and the lower face 11L. The electrode terminal 12HU is electrically connected via solder 15 to an image-sensing device electrode 42U (42) of the solid-state image sensing device 40 which will be described later. The electrode terminal 12HL is electrically connected to an image-sensing device electrode 42L (42) of the solid-state image sensing device 40 via the solder 15.

A center conductor terminal 12I (first cable terminal) and an external conductor terminal 12J (first cable terminal) are formed on one surface of the first substrate main body 11, that is, on the upper face 11U. The center conductor terminal 12I and the external conductor terminal 12 are electrically connected to the upper face wiring 12U. The center conductor terminal 12I is electrically connected via solder 16 to a center conductor 31 of the signal cable 30 which will be described later. The external conductor terminal 12J is electrically connected via solder 17 to an external conductor 33 of the signal cable 30.

Upper face resists 13A and 13B (13) are formed on the upper face 11U of the first substrate main body 11 so as to coat a surface of the upper face wiring 12U. The upper face resist 13A is formed between the solder 15 and the solder 16. The upper face resist 13B is formed between the solder 16 and the solder 17. A lower face resist 13C (13) is formed on the lower face 11L of the first substrate main body 11 so as to coat a surface of the lower face wiring 12L.

In FIG. 1, as seen in the direction from the solid-state image sensing device 40 toward the inner end face 11F, the signal cable 30 is disposed within an outline of the solid-state image sensing device 40 on a plane of projection, and the signal cable 30 does not partially protrude from the outline of the solid-state image sensing device 40 shown in the plane of projection of the solid-state image sensing device 40.

Note that, a resin mold may be formed on the upper face 11U of the first substrate main body 11 so as to coat the solder 15, 16, and 17, the center conductor 31 and the external conductor 33 of the signal cable 30, and the upper face resists 13A and 13B. By forming the resin mold on the upper face 11U as stated above, it is possible to increase the strength of the first substrate main body 11.

Moreover, a resin mold may be formed on the lower face 11L of the first substrate main body 11 so as to coat the solder 15 and the lower face resist 13C. By forming the resin mold on the lower face 11L as stated above, it is possible to increase the strength of the first substrate main body 11.

Furthermore, a resin mold may be formed on both surfaces of the first substrate main body 11. In this case, it is possible to further increase the strength of the first substrate main body 11 by the resin mold formed on both surfaces.

Particularly, as an example, one or more embodiments of the invention show the configuration in which the center conductor terminal 12I and the external conductor terminal 12J are formed on the upper face 11U serving as one of the surfaces of the first substrate main body 11; however, the invention is not limited to this configuration. The center conductor terminal 12I and the external conductor terminal 12J may be formed on the lower face 11L serving as the other surface of the first substrate main body 11. In this case, a wiring structure is adopted in which a center conductor terminal and an external conductor terminal formed on the lower face 11L are connected to the center conductor 31 and the external conductor 33, respectively.

Furthermore, the invention is not limited to a structure in which the center conductor terminal 12I and the external conductor terminal 12J are formed only on one of the surfaces of the first substrate main body 11. A structure may be adopted in which conductor terminals are formed on both surfaces of the first substrate main body 11, that is, on the upper face 11U and the lower face 11L, and the center conductor 31 and the external conductor 33 are connected to the conductor terminals. In addition, in the structure in which the conductor terminals are formed on both surfaces of the first substrate main body 11, a wiring structure may be adopted in which the through electrode 14 is not formed depending on a wiring pattern.

As a configuration in which conductor terminals are formed on both surfaces of the first substrate main body 11, for example, a configuration is adopted in which, a center conductor terminal and an external conductor terminal to which a center conductor 31A and an external conductor 33A of a first coaxial cable 30A (which will be described later) are connected, respectively, are formed on the upper face 11U, and a center conductor terminal and an external conductor terminal to which a center conductor 31B and an external conductor 33B of a second coaxial cable 30B (which will be described later) are connected, respectively, are formed on the lower face 11L.

Additionally, a structure may be adopted in which a center conductor terminal is provided on one of the upper face 11U and the lower face 11L and an external conductor terminal is provided on the other face.

(Second Substrate 20)

The second substrate 20 includes a second substrate main body 21 serving as an insulating member and a second wiring 22 formed on the second substrate main body 21. The second substrate main body 21 has an upper face 21U (first surface) and a lower face 21L (second surface) opposite to the upper face 21U. An upper face wiring 22U forming the second wiring 22 is formed on the upper face 21U. A lower face wiring 22L forming the second wiring 22 is formed on the lower face 21L. The second wiring 22 includes a conductive wiring pattern formed on both the upper face 21U and the lower face 21L. The wiring pattern will be described later. Particularly, in one or more embodiments of the invention, the number of second substrates 20 is not two or more but is one.

Furthermore, the second substrate 20 includes a through electrode 28 that penetrates through the second substrate main body 21 between the upper face 21U and the lower face 21L. The through electrode 28 electrically connects the upper face wiring 22U to the lower face wiring 22L. A structure of the through electrode 28 will be described later.

Moreover, the second substrate 20 includes a center conductor terminal 22I (second cable terminal), an external conductor terminal 22J (second cable terminal), and a shield terminal 22K (second cable terminal). The center conductor terminal 22I, the external conductor terminal 22J, and the shield terminal 22K are formed on one of the surfaces of the second substrate 20, that is, on the upper face 21U, and are electrically connected to the second wiring 22.

The center conductor terminal 22I is electrically connected via solder 26 to the center conductor 31 of the signal cable 30. The external conductor terminal 22J is electrically connected via solder 27 to the external conductor 33 of the signal cable 30. The shield terminal 22K is electrically connected via solder 29 to a shield conductor 30C of the signal cable 30.

Resists 23A and 23B (23) are formed on the upper face 21U of the second substrate main body 21 so as to coat a surface of the second wiring 22. The resist 23B is formed between the solder 26 and the solder 27. The resist 23A is formed close to the solder 26 on the center conductor terminal 22I.

The second substrate main body 21 has an inner end face 21F, an outer end face 21E (end face), and two attachment holes 25 provided close to the outer end face 21E. The attachment holes 25 are portions to which a jig such as wire is attached when the imaging module 1 is attached to a catheter. In a state where the jig is attached to the attachment holes 25, by inserting the jig into a tube forming the catheter and drawing the jig into the tube, it is possible to dispose the second substrate 20 inside the tube. The details will be described with reference to FIG. 9.

Additionally, on the upper face 21U or the lower face 21L of the second substrate main body 21, Identification Number used for individual identification of the imaging module 1 may be represented at the portion adjacent to the position at which the attachment holes 25 are formed.

The second substrate 20 includes an external connection terminal 24 formed on the second substrate main body 21, and the external connection terminal 24 is electrically connected to the second wiring 22. The external connection terminal 24 is connected to an external device. Note that, the external connection terminal 24 and the second wiring 22 are simultaneously formed on the second substrate main body 21.

Particularly, as an example, one or more embodiments of the invention show the configuration in which the center conductor terminal 22I and the external conductor terminal 22J are formed on the upper face 21U serving as one of the surfaces of the second substrate main body 21; however, the invention is not limited to this configuration. The center conductor terminal 22I and the external conductor terminal 22J may be formed on the lower face 21L serving as the other surface of the second substrate main body 21. In this case, a wiring structure is adopted in which a center conductor terminal and an external conductor terminal formed on the lower face 21L are connected to the center conductor 31 and the external conductor 33, respectively.

Furthermore, the invention is not limited to a structure in which the center conductor terminal 22I and the external conductor terminal 22J are formed only on one of the surfaces of the second substrate main body 21. A structure may be adopted in which conductor terminals are formed on both surfaces of the second substrate main body 21, that is, on the upper face 21U and the lower face 21L, and the center conductor 31 and the external conductor 33 are connected to the conductor terminals. In addition, in the structure in which the conductor terminals are formed on both surfaces of the second substrate main body 21, a wiring structure may be adopted in which the through electrode 28 is not formed depending on a wiring pattern.

As a configuration in which conductor terminals are formed on both surfaces of the second substrate main body 21, for example, a configuration is adopted in which, a center conductor terminal and an external conductor terminal to which a center conductor 31A and an external conductor 33A of a first coaxial cable 30A (which will be described later) are connected, respectively, are formed on the upper face 21U, and a center conductor terminal and an external conductor terminal to which a center conductor 31B and an external conductor 33B of a second coaxial cable 30B (which will be described later) are connected, respectively, are formed on the lower face 21L.

Additionally, a structure may be adopted in which a center conductor terminal is provided on one of the upper face 21U and the lower face 21L and an external conductor terminal is provided on the other face.

(Solid-State Image Sensing Device 40 and Lens Housing 50)

The solid-state image sensing device 40 includes a light-receiving face 41, an electrode surface 43 located on the opposite side of the light-receiving face 41, and the image-sensing device electrodes 42U and 42L (two image-sensing device electrodes) provided on the electrode surface 43. The first substrate 10 is connected to the electrode surface 43 so that the outer end face 11E of the first substrate main body 11 is located between the image-sensing device electrodes 42U and 42L.

In a state where the outer end face 11E of the first substrate 10 is connected to the electrode surface 43 of the solid-state image sensing device 40, the image-sensing device electrode 42U has a surface parallel to the direction substantially orthogonal to the electrode terminal 12HU, and the image-sensing device electrode 42L has a surface parallel to the direction substantially orthogonal to the electrode terminal 12HL. In this configuration, the solder 15 connects the image-sensing device electrode 42U and the electrode terminal 12HU which are substantially orthogonal to each other, and connects the image-sensing device electrode 42L and the electrode terminal 12HL which are substantially orthogonal to each other.

FIG. 1 shows the image-sensing device electrodes 42U and 42L which are arranged at the upper position and the lower position, respectively; however, when seen in a plan view of the electrode surface 43 (in a plan view showing the electrode surface 43 when viewed in a vertical direction) four image-sensing device electrodes 42 are arranged on the electrode surface 43. That is, two image-sensing device electrodes 42U and two image-sensing device electrodes 42L are formed on the electrode surface 43.

The lens housing 50 is connected to the light-receiving face 41, and a lens unit such as an object lens is mounted on the lens housing 50. As the solid-state image sensing device 40, for example, a CMOS (complementary metal oxide semiconductor) may be used.

(Signal Cable 30)

Figure 2:
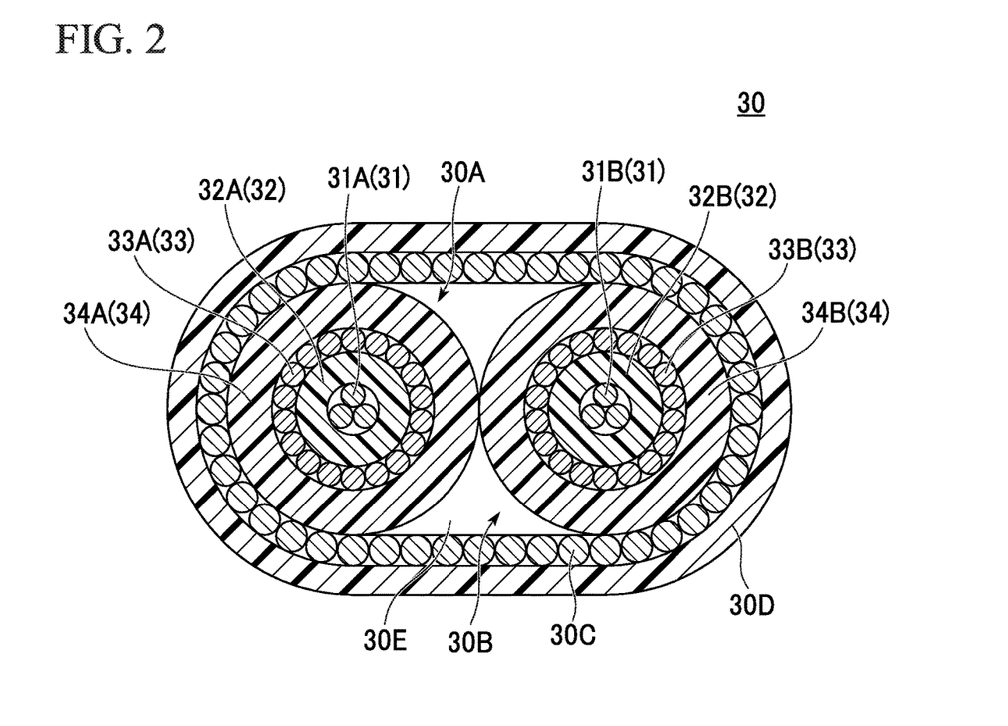
FIG. 2 is a cross-sectional view showing a signal cable of the imaging module according to one or more embodiments of the invention.

FIG. 2 is a cross-sectional view showing the signal cable 30 of the imaging module according to one or more embodiments of the invention.

The signal cable 30 is provided between the first substrate 10 and the second substrate 20 and includes two coaxial cable (signal line, a first coaxial cable 30A, a second coaxial cable 30B), a shield conductor 30C that surrounds the first coaxial cable 30A and the second coaxial cable 30B, and an outer coating 30D that surrounds the shield conductor 30C. The shield conductor 30C is provided on the entire inner peripheral surface of the outer coating 30D and is formed in a layer shape.

In FIG. 2, for example, the structure is shown in which the shield conductor 30C is disposed separately from a cable contact portion at which the side portions of the first coaxial cable 30A and the second coaxial cable 30B are in contact with each other, and a space 30E is present between the cable contact portion and the shield conductor 30C located at both sides of the cable contact portion. However, as a cross-sectional structure of the signal cable 30, a cross-sectional structure is applicable, in which the shield conductor 30C enters a region of the space 30E shown in FIG. 2 and a space is substantially absent among the first coaxial cable 30A, the second coaxial cable 30B, and the layer-shaped shield conductor 30C.

Each of the coaxial cables 30A and 30B includes a center conductor 31 (31A, 31B), an internal insulator 32 (32A, 32B), an external conductor 33 (33A, 33B), and an external insulator 34 (34A, 34B). For example, the center conductor 31 is used as a signal line that supplies a signal to the solid-state image sensing device 40, and the external conductor 33 is used as a power supply line that supplies electric power to the solid-state image sensing device 40.

The center conductor 31 (31A, 31B) electrically connects the center conductor terminal 12I of the first substrate 10 to the center conductor terminal 22I of the second substrate 20.

The external conductor 33 (33A, 33B) electrically connects the external conductor terminal 12J of the first substrate 10 to the external conductor terminal 22J of the second substrate 20.

The shield conductor 30C and the outer coating 30D surrounds the first coaxial cable 30A and the second coaxial cable 30B over the entire signal cable 30. The shield conductor 30C and the outer coating 30D are removed at the position close to the first substrate 10 (the position close to the inner end face 11F shown in FIG. 1), and the first coaxial cable 30A and the second coaxial cable 30B are exposed. On the other hand, the outer coating 30D is removed at the position close to the second substrate 20 (the position close to the inner end face 21F shown in FIG. 1), and the shield conductor 30C is exposed, and the shield conductor 30C is electrically connected to the shield terminal 22K via the solder 29. In this configuration, the shield terminal is connected to, for example, GND, and therefore the shield conductor 30C is grounded.

Furthermore, as shown in FIG. 1, the external conductor 33 and the center conductor 31 which constitute each of the first coaxial cable 30A and the second coaxial cable 30B are exposed so as to correspond to wiring patterns of the first substrate 10 and the second substrate 20. Specifically, between the solder 27 and the solder 29, the external conductor 33 (33A, 33B) is exposed from the external insulator 34 (34A, 34B). The exposed external conductor 33 (33A, 33B) is electrically connected to the external conductor terminal 22J via the solder 27. Between the solder 27 and the solder 26, the center conductor 31 (31A, 31B) is exposed from the internal insulator 32 (32A, 32B). The exposed center conductor 31 (31A, 31B) is electrically connected to the center conductor terminal 22I via the solder 26.

(Positional Relationship Among First Substrate 10, Second Substrate 20, and Signal Cable 30)

Figure 3:
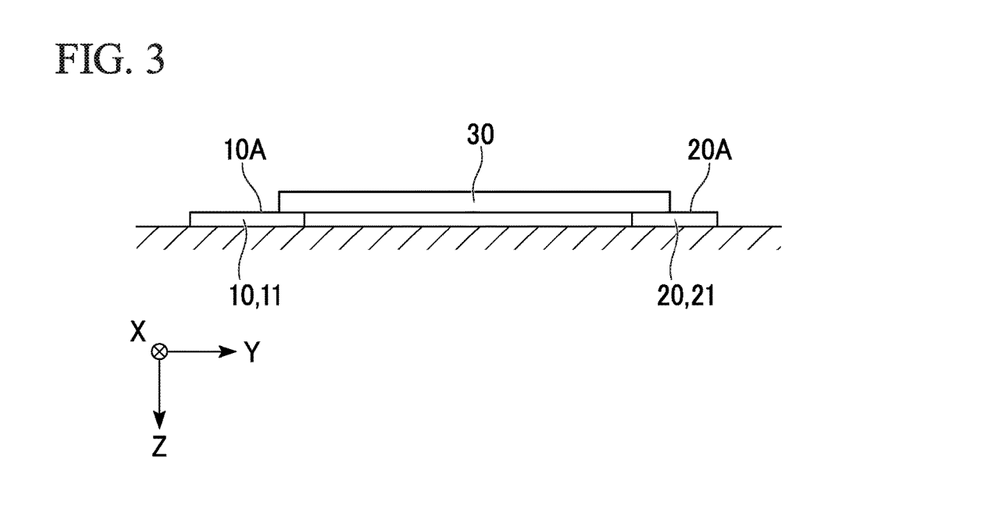
FIG. 3 is a view showing a schematic configuration of the imaging module according to one or more embodiments of the invention and is an explanatory view showing a positional relationship among a first substrate, a second substrate, and a signal cable.

FIG. 3 is a view showing a schematic configuration of the imaging module according to one or more embodiments of the invention and is an explanatory view showing a positional relationship among the first substrate 10, the second substrate 20, and the signal cable 30.

As shown in FIG. 3, in a state where the first substrate 10 and the second substrate 20 are on the same horizontal plane, the surface 10A (upper face 11U) on which the first cable terminal is connected to the signal cable 30 and the surface 20A (upper face 21U) on which the second cable terminal is connected to the signal cable 30 are located on the same plane. Furthermore, the first substrate 10 is connected to the second substrate 20 with the signal cable 30 interposed therebetween so that one signal cable 30 corresponds to a pair of the first substrate 10 and the second substrate 20.

In the imaging module 1, in a state where the signal cable 30 extends straight without torsional deformation, the surface 10A on which the center conductor terminal 12I and the external conductor terminal 12J of the first substrate 10 are formed is referred to as an upper face, a surface opposite to the surface 10A is referred to as a lower face, the surface 20A on which the center conductor terminal 22I and the external conductor terminal 22J of the second substrate 20 are formed is referred to as an upper face, and a surface opposite to the surface 20A is referred to as a lower face.

Accordingly, as shown in FIG. 3, in a state where the lower face of each of the first substrate 10 and the second substrate 20 are in contact with the same horizontal plane, the first substrate 10 and the second substrate 20 can be mounted on the same horizontal plane. As shown in FIG. 3, when the lower faces of the first substrate 10 and the second substrate 20 are in contact with the same horizontal plane and are mounted on the same horizontal plane, the signal cable 30 is located at the upper side of the first substrate 10 and the second substrate 20.

In this configuration, in a state where the first substrate main body 11 constituting the first substrate 10 and the second substrate main body 21 constituting the second substrate 20 are fixed on the same horizontal plane, the signal cable 30 can be connected to each of the surfaces 10A and 20A by soldering, and it is possible to simplify a step of manufacturing the imaging module 1.

Furthermore, in order to effectively mass-produce the imaging module 1, regarding a plurality of pairs of the first substrate 10 and the second substrate 20 and a plurality of signal cables 30, it is necessary to collectively connect the pairs of the first substrate 10 and the second substrate 20 to the plurality of the signal cables 30 by soldering so that one signal cable 30 corresponds to each pair of the first substrate 10 and the second substrate 20.

In this case, in a state where the surface 10A of the first substrate 10 and the surface 20A of the second substrate 20 are located on the same plane and in a state where the plurality of pairs of the first substrate 10 and the second substrate 20 are arranged to align in the X-direction (in a direction vertical to the paperface shown in FIG. 3), it is possible to collectively connect the plurality of the signal cables 30 to the plurality of pairs of the first substrate 10 and the second substrate 20.

In the above-described connection step, since the surface 10A of the first substrate 10 and the surface 20A of the second substrate 20 are arranged on the same plane, it is possible to supply solder to the surfaces 10A and 20A so as to be directed in the Z-direction (direction of gravitational force), and it is thereby possible to increase the manufacturing efficiency in the mass production line of the imaging module 1.

As a result of arranging the surface 10A of the first substrate 10 and the surface 20A of the second substrate 20 on the same plane, it is not necessary to flip the first substrate 10 or the second substrate 20, and also it is not necessary to supply solder to a back surface of the substrate (in the direction opposite to the direction of gravitational force, in the direction that is indicated by the arrow and is opposite to the Z-direction). Accordingly, it is possible to achieve both mass production and simplification of production step of the imaging module 1.

Note that, not only in the case of collectively connecting the plurality of pairs of the first substrate 10 and the second substrate 20 to the plurality of the signal cables 30 by soldering, but also in the case of sequentially connecting the signal cable 30 to each of the pairs of the first substrate 10 and the second substrate 20, it is not necessary to flip the first substrate 10 or the second substrate 20, and it is possible to increase the manufacturing efficiency in the mass production line of the imaging module 1.

(Relationship in Size Among Solid-State Image Sensing Device 40, Second Substrate 20, and Signal Cable 30)

Figure 4:
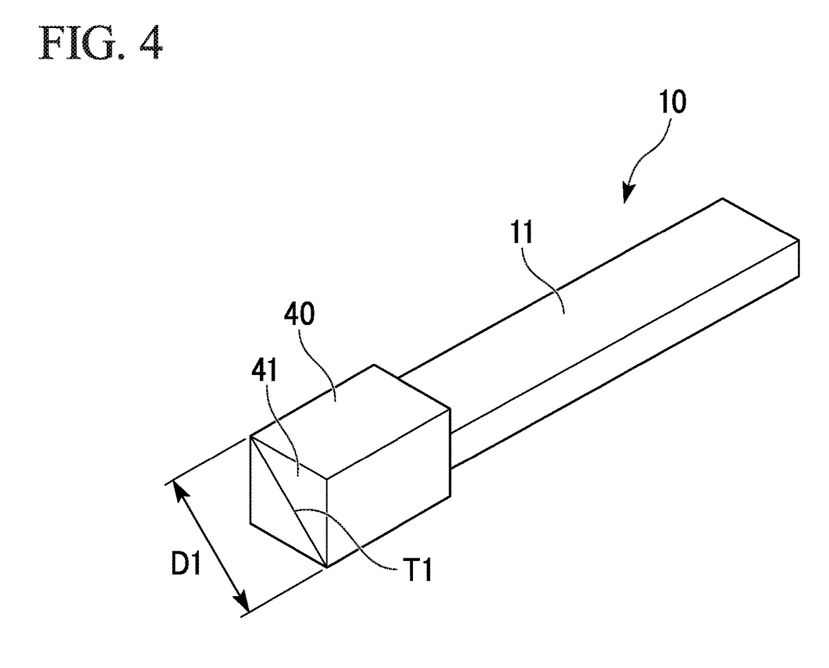
FIG. 4 is a perspective view showing a light-receiving face of a solid-state image sensing device of the imaging module according to one or more embodiments of the invention.
Figure 5A:
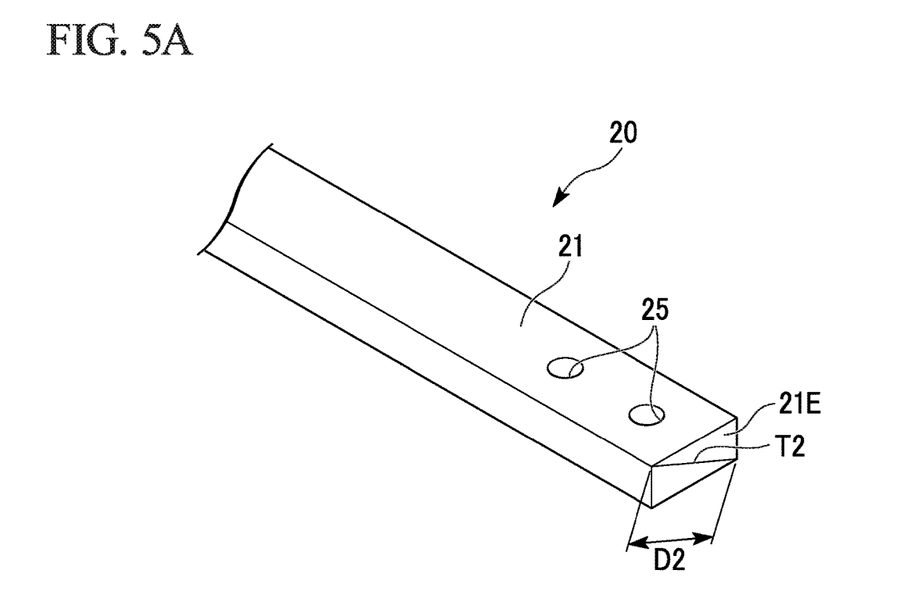
FIG. 5A is a perspective view showing an end of a second substrate of the imaging module according to one or more embodiments of the invention.
Figure 5B:
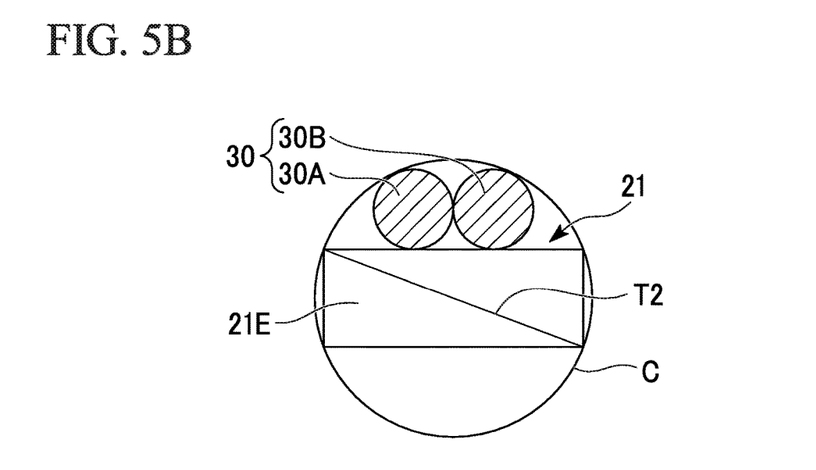
FIG. 5B is a side view showing an end of a second substrate of the imaging module according to one or more embodiments of the invention.

FIG. 4 is a perspective view showing a light-receiving face of the solid-state image sensing device of the imaging module according to one or more embodiments of the invention. FIG. 5A is a perspective view showing an end of the second substrate of the imaging module according to one or more embodiments of the invention. FIG. 5B is a side view showing an end of the second substrate of the imaging module according to one or more embodiments of the invention.

Note that, in FIG. 4, the wiring structure of the first substrate 10 shown in FIG. 1 (i.e., the first wiring 12 formed on the first substrate main body 11, the solder 15 to 17, the signal cable 30 connected to the first substrate 10, and the lens housing 50) is omitted. In FIG. 5A, the wiring structure the second substrate 20 shown in FIG. 1 (i.e., the second wiring 22 formed on the second substrate main body 21, the solder 26, 27, the signal cable 30 connected to the second substrate 20) is omitted. The second substrate 20 and the signal cable 30 connected to a surface of the second substrate 20 are shown in FIG. 5B.

In the case where a length of a first diagonal line T1 on the light-receiving face 41 of the solid-state image sensing device 40 is defined as D1 and a length of a second diagonal line T2 on the outer end face 21E of the second substrate main body 21 is defined as D2, the length D2 is less than or equal to the length D1 (condition D1≥D2 is satisfied). Here, the length of the first diagonal line T1 means the distance between two corners that are located at the positions opposite to each other on the light-receiving face 41. Similarly, the length of the second diagonal line T2 means the distance between two corners that are opposite to each other on the outer end face 21E.

In addition, as shown in FIG. 5B, the signal cable 30 is arranged inside the circumscribed circle C of the second substrate main body 21. The diameter of the circumscribed circle C corresponds to the length D2 of the second diagonal line T2.

(Wiring Pattern on Second Substrate 20)

Figure 6A:
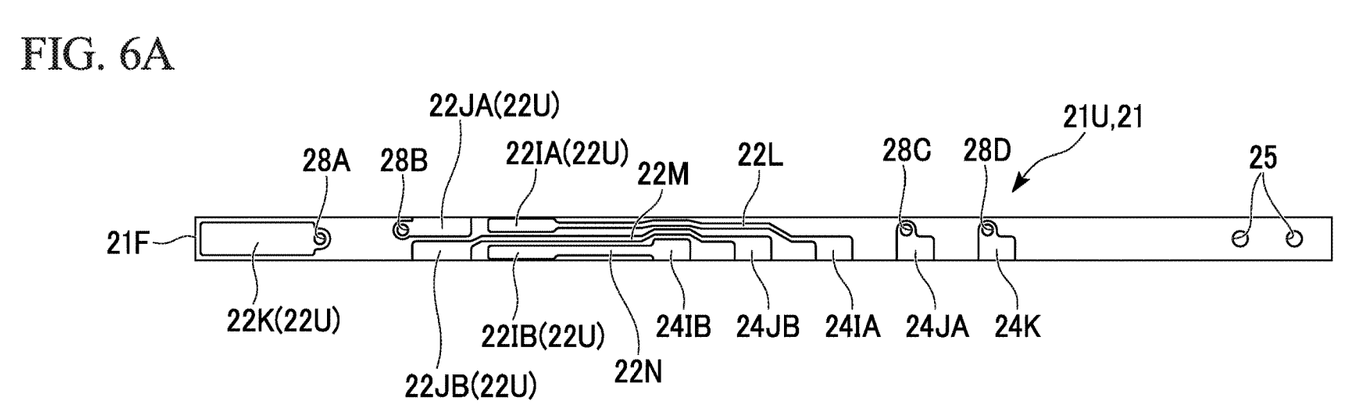
FIG. 6A is a plan view showing a wiring pattern formed on the second substrate of the imaging module according to one or more embodiments of the invention and is an explanatory view showing a connection structure between the image-sensing device and the signal cable.
Figure 6B:
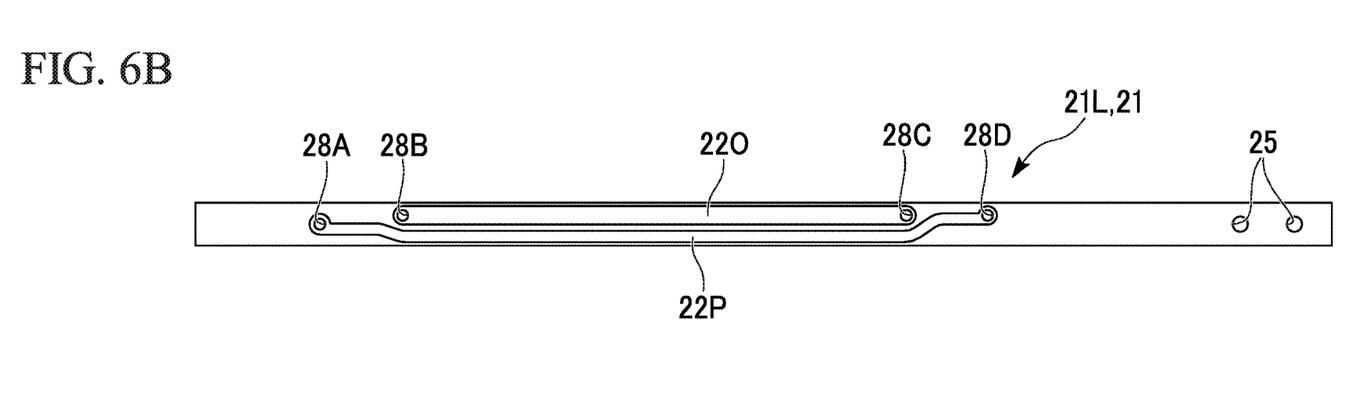
FIG. 6B is a plan view showing a wiring pattern formed on the second substrate of the imaging module according to one or more embodiments of the invention and is an explanatory view showing a connection structure between the image-sensing device and the signal cable.

FIGS. 6A and 6B are views each showing a wiring pattern formed on the second substrate of the imaging module according to one or more embodiments of the invention. FIG. 6A shows a wiring pattern of the upper face wiring 22U formed on the upper face 21U of the second substrate main body 21. FIG. 6B shows a wiring pattern of the lower face wiring 22L formed on the lower face 21L of the second substrate main body 21. Note that, FIG. 6B is not a bottom view showing the lower face 21L but is a projection view as seen from the upper face 21U shown in FIG. 6A.

Note that, the resists 23A and 23B are formed on the upper face 21U of the second substrate main body 21 shown in FIG. 1; however, the resists 23A and 23B are omitted in FIGS. 6A and 6B.

As shown in FIG. 6A, reference numeral 22JA corresponds to the external conductor terminal 22J and is a terminal connected to the external conductor 33A of the first coaxial cable 30A via the solder 27. Hereinbelow, it will be referred to as an external conductor terminal 22JA. Reference numeral 22JB corresponds to the external conductor terminal 22J and is a terminal connected to the external conductor 33B of the second coaxial cable 30B via the solder 27. Hereinbelow, it will be referred to as an external conductor terminal 22JB.

Reference numeral 22IA corresponds to the center conductor terminal 22I and is a terminal connected to the center conductor 31A of the first coaxial cable 30A via the solder 26. Hereinbelow, it will be referred to as a center conductor terminal 22IA. Reference numeral 22IB corresponds to the center conductor terminal 22I and is a terminal connected to the center conductor 31B of the second coaxial cable 30B via the solder 26. Hereinbelow, it will be referred to as a center conductor terminal 22IB. Reference numeral 22K represents a terminal that is provided at the position adjacent to the inner end face 21F of the second substrate main body 21 and is connected to the shield conductor 30C. Hereinbelow, it will be referred to as a shield terminal 22K.

Reference numerals 24K, 24IB, 24IA, 24JA, and 24JB represent external connection terminals formed on the upper face 21U and correspond to the external connection terminal 24 shown in FIG. 1. The external connection terminals 24K, 24IB, 24IA, 24JA, and 24JB align in the extending direction of the second substrate main body 21.

Reference numeral 22L represents a drawing wiring that connects the center conductor terminal 22IA to the external connection terminal 24IA. Reference numeral 22M represents a drawing wiring that connects the external conductor terminal 22JB to the external connection terminal 24JB. Reference numeral 22N represents a drawing wiring that connects the center conductor terminal 22IB to the external connection terminal 24IB.

The drawing wiring 22N is a wiring having a linear part that extends straight in the extending direction of the second substrate main body 21.

The drawing wiring 22M is a wiring having a linear part that extends straight in the extending direction of the second substrate main body 21 and a bending part that bends so as to follow the shape of the external connection terminal 24IB.

The drawing wiring 22L is a wring having a wiring part that extends straight in the extending direction of the second substrate main body 21 and a bending part that bends so as to follow the shape of the drawing wiring 22M.

Reference numerals 28A, 28B, 28C, and 28D are each a through electrode correspond to the through electrode 28 shown in FIG. 1. Through electrode 28A is connected to the shield terminal 22K, the through electrode 28B is connected to the external conductor terminal 22JA, the through electrode 28C is connected to the external connection terminal 24JA, and the through electrode 28D is connected to the external connection terminal 24K.

On the other hand, as shown in FIG. 6B, the lower face wiring 22L formed on the lower face 21L has drawing wirings 22O and 22P. The drawing wiring 22O connects the through electrode 28B to the through electrode 28C. The drawing wiring 22P connects the through electrode 28A to the through electrode 28D.

The external conductor terminals, the center conductor terminals, the external connection terminals, and the drawing wirings which are described above can be collectively formed by patterning using a known photolithographic technique or the like. Furthermore, the through electrodes 28A, 28B, 28C, and 28D can also be formed by a known method.

As the upper face wiring 22U and the lower face wiring 22L have the aforementioned wiring structure, even in the case where a width of the second substrate main body 21 (a length in the direction orthogonal to the extending direction) is small, the external conductor terminals and the center conductor terminals of the coaxial cable 30 (first coaxial cable 30A, second coaxial cable 30B) can be connected to the external connection terminals 24K, 24IB, 24IA, 24JA, and 24JB, and it is possible to easily connect the terminals to the external device.

Note that, the wiring pattern formed on the second substrate 20 is not limited to the structure shown in FIGS. 6A and 6B. For example, a wiring structure shown in FIGS. 7A and 7B can be adopted.

(Modified Example of Wiring Pattern on Second Substrate 20)

Figure 7A:
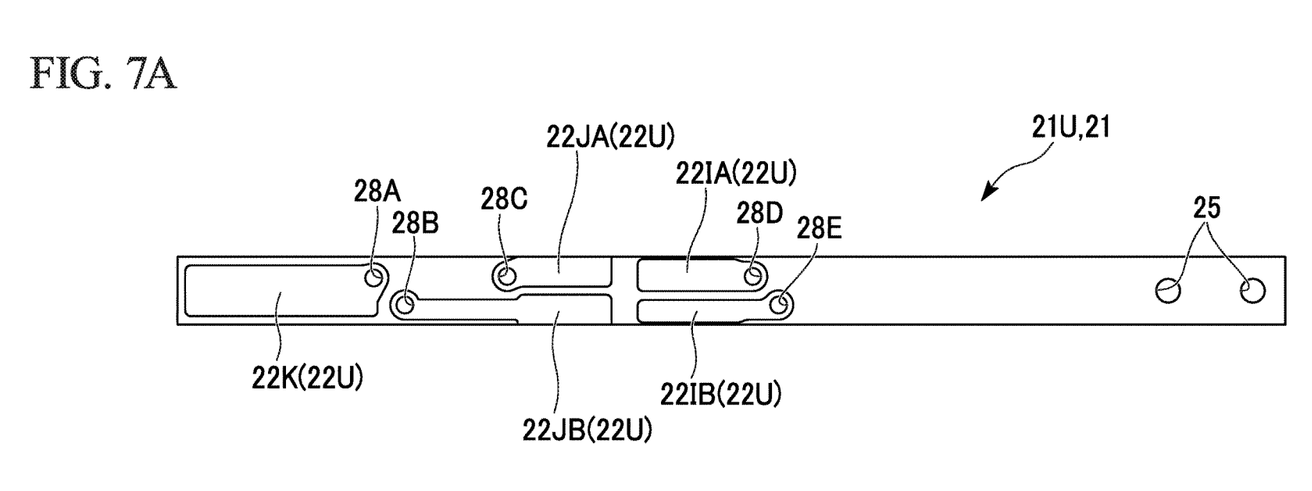
FIG. 7A is a plan view showing a wiring pattern formed on the second substrate of an imaging module according to a modified example of one or more embodiments of the invention and is an explanatory view showing a connection structure between the image-sensing device and the signal cable.
Figure 7B:
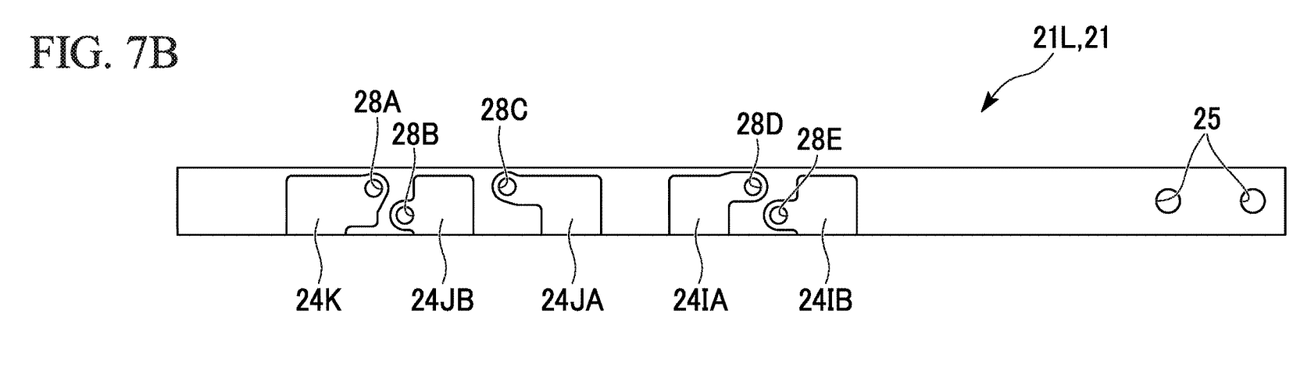
FIG. 7B is a plan view showing a wiring pattern formed on the second substrate of an imaging module according to a modified example of one or more embodiments of the invention and is an explanatory view showing a connection structure between the image-sensing device and the signal cable.

FIGS. 7A and 7B are views each showing a wiring pattern formed on the second substrate of the imaging module according to a modified example of one or more embodiments of the invention. FIG. 7A shows a wiring pattern of the upper face wiring 22U formed on the upper face 21U of the second substrate main body 21. FIG. 7B shows a wiring pattern of the lower face wiring 22L formed on the lower face 21L of the second substrate main body 21. Note that, FIG. 7B is not a bottom view showing the lower face 21L but is a projection view as seen from the upper face 21U shown in FIG. 7A.

Note that, the resists 23A and 23B are formed on the upper face 21U of the second substrate main body 21 shown in FIG. 1; however, the resists 23A and 23B are omitted in FIGS. 7A and 7B. In FIGS. 7A and 7B, identical reference numerals are used for the elements that are identical to those of FIGS. 6A and 6B, and the explanations thereof are omitted or simplified here.

As shown in FIG. 7A, on the upper face 21U, the shield terminal 22K is connected to the through electrode 28A, the external conductor terminal 22JB is connected to the through electrode 28B, the external conductor terminal 22JA is connected to the through electrode 28C, the center conductor terminal 22IA is connected to the through electrode 28D, the center conductor terminal 22IB is connected to the through electrode 28E.

On the other hand, as shown in FIG. 7B, on the lower face 21L, the external connection terminals 24K, 24JB, 24JA, 24IA, and 24IB align in the extending direction of the second substrate main body 21.

The external connection terminal 24K is connected to the shield terminal 22K through the through electrode 28A. The external connection terminal 24JB is connected to the external conductor terminal 22JB through the through electrode 28B. The external connection terminal 24JA is connected to the external conductor terminal 22JA through the through electrode 28C. The external connection terminal 24IA is connected to the center conductor terminal 22IA through the through electrode 28D. The external connection terminal 24IB is connected to the center conductor terminal 22IB through the through electrode 28E.

As the upper face wiring 22U and the lower face wiring 22L have the aforementioned wiring structure, even in the case where a width of the second substrate main body 21 (a length in the direction orthogonal to the extending direction) is small, the external conductor terminals and the center conductor terminals of the coaxial cable 30 (first coaxial cable 30A, second coaxial cable 30B) can be connected to the external connection terminals 24K, 24JB, 24JA, 24IA, and 24IB, and it is possible to easily connect the terminals to the external device.

Moreover, since it is possible to connect the terminals formed on the upper face 21U to the terminals formed on the lower face 21L through the through electrodes without using a drawing wiring having a bending part, it is possible to achieve a simplified wiring structure.

According to one or more embodiments of the invention, the condition D condition D1≥D2 is satisfied, furthermore, the signal cable 30 is disposed inside the circumscribed circle C of the second substrate main body 21, and the circumscribed circle C has a diameter corresponding to the length of the second diagonal line T2. Because of this, the second substrate 20 can be smaller than the solid-state image sensing device 40. Also, when the imaging module 1 is attached to a medical instrument such as a catheter, firstly, the second substrate 20 is inserted into a hole to which the solid-state image sensing device 40 is to be attached, and the imaging module 1 can be easily drawn into the medical instrument.

On the other hand, in the case where D2 is larger than D1, it is necessary to push the imaging module into the medical instrument from the rear thereof or a size of a hole to which a solid-state image sensing device is to be attached is necessary to be larger than D2. In the case of pushing the imaging module into the medical instrument from the rear thereof, the imaging module is pushed into the inside of the medical instrument by utilizing the rigidity of a signal cable. However, in the case where the signal cable is elastic, it is not possible to effectively push the imaging module into the inside of the medical instrument, and workability therefor becomes deteriorated. In the case where a size of a hole to which the solid-state image sensing device is to be attached is larger than D2, the entire size of the medical instrument becomes larger accordingly, and therefore it is not possible to reduce the medical instrument in size. In contrast, according to the imaging module 1 of one or more embodiments of the invention, it is possible to overcome an issue that may occur when D2 is larger than D1.

Figure 8:
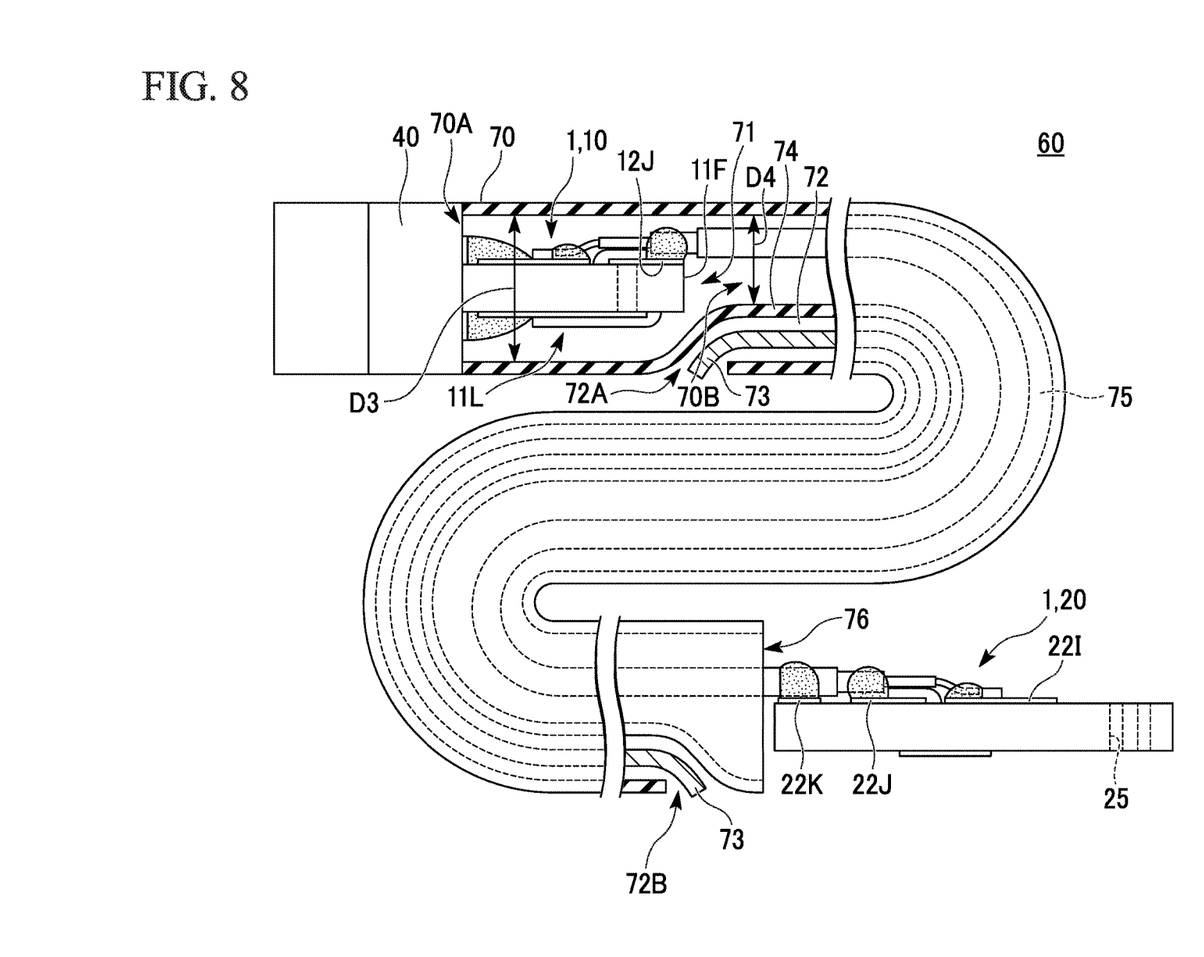
FIG. 8 is a partial cross-sectional view showing a schematic configuration of an imaging-module-attached catheter according to one or more embodiments of the invention.

FIG. 8 is a partial cross-sectional view showing a schematic configuration of a catheter 60 according to one or more embodiments of the invention.

In FIG. 8, identical reference numerals are used for the elements that are identical to those of the above-mentioned one or more embodiments of the invention, and the explanations thereof are omitted or simplified here. The catheter 60 shown in FIG. 8 is an imaging-module-attached catheter including the above-mentioned imaging module 1.

In the following explanation regarding the catheter 60, the position at which the solid-state image sensing device 40 or the first substrate 10 is disposed may be referred to as a front side, and the position at which the second substrate 20 is disposed may be referred to as a rear side.

The catheter 60 includes a tube 70 that is made of, for example, silicon or the like and has an insulation property. In one or more embodiments of the invention, silicon is adopted as a material used to form the tube 70, a flexible material or a metal material other than silicon may be used.

For example, as a flexible material, silicon, polyurethane, polyethylene, polytetrafluoroethylene (PTFE, for example, Teflon (registered trademark)), or the like is adopted. As a metal material, titanium, a titanium alloy, a stainless steel, or the like is adopted. Additionally, it is not limited to a flexible material or a metal material, ceramic material may be used as a material used to form the tube 70.

The tube 70 includes a module insertion opening 70A, a cable insertion opening 70B, a module arrangement region 71 in which the first substrate 10 and part of the signal cable 30 which form the imaging module 1 are disposed, a channel 72, a cable arrangement region 75, and a second substrate output port 76.

Specifically, in a step of manufacturing the catheter 60, the module insertion opening 70A is an opening through which the imaging module 1 is inserted into the tube 70, the cable insertion opening 70B is an opening into which the second substrate 20 and the signal cable 30 which form the imaging module 1 are inserted, the cable arrangement region 75 is a tube through which the second substrate 20 passes, and the second substrate output port 76 is an opening through which the second substrate 20 is extracted from the tube 70.

The manufacturing steps described above are carried out, as a result, the solid-state image sensing device 40 is attached to the module insertion opening 70A, the first substrate 10 and part of the signal cable 30 are disposed in the module arrangement region 71, the signal cable 30 is disposed in the cable arrangement region 75, and the second substrate 20 is disposed outside the second substrate output port 76.

The tube 70 has a front opening 72A located close to the first substrate 10 and a rear opening 72B located close to the second substrate 20, and the pathway formed between the front opening 72A and the rear opening 72B is the channel 72. The channel 72 is located between the external conductor terminal 12J (first cable terminal) and the external conductor terminal 22J (second cable terminal) and is disposed adjacent to the cable arrangement region 75. The channel 72 is isolated from the cable arrangement region 75 by an inner wall 74. The channel 72 is disposed within an outline of the solid-state image sensing device 40 on a plane of projection as seen in a direction from the solid-state image sensing device 40 to the inner end face 11F.

Next, an internal diameter of the module insertion opening 70A and an internal diameter of the cable insertion opening 70B (cable arrangement region 75) will be described.

As described above, in the case where the length of the first diagonal line T1 on the light-receiving face 41 of the solid-state image sensing device 40 is defined as D1 and a length of the second diagonal line T2 on the outer end face 21E of the second substrate main body 21 is defined as D2, an internal diameter D3 of the module insertion opening 70A is set less than or equal to the length D1 and larger than or equal to the length D2 (condition D1≥D3≥D2 is satisfied).

Furthermore, an internal diameter D4 of the cable insertion opening 70B (cable arrangement region 75) is set less than or equal to the length D3 and larger than or equal to the length D2 (condition D3≥D4≥D2).

That is, in the relationship of the lengths D1, D2, D3, and D4, condition D1≥D3≥D4≥D2 is satisfied.

In other cases, the channel 72 may be used as a lumen and may be used as a working channel. In the case of using the channel 72 as a lumen, for example, a solvent medium injection lumen that ejects a solvent medium toward the front of the catheter 60 or a vacuuming lumen that removes liquid present in front of the catheter 60 can be provided in the tube 70.

Additionally, in the case of using the channel 72 as the working channel, for example, a treatment tool indicated by reference numeral 73 may be inserted into the channel 72. As the treatment tool 73, for example, various forcipes, a snare, a guide wire, a stent, a laser treatment tool, a high-frequency treatment tool, or the like is adopted.

Figure 9:
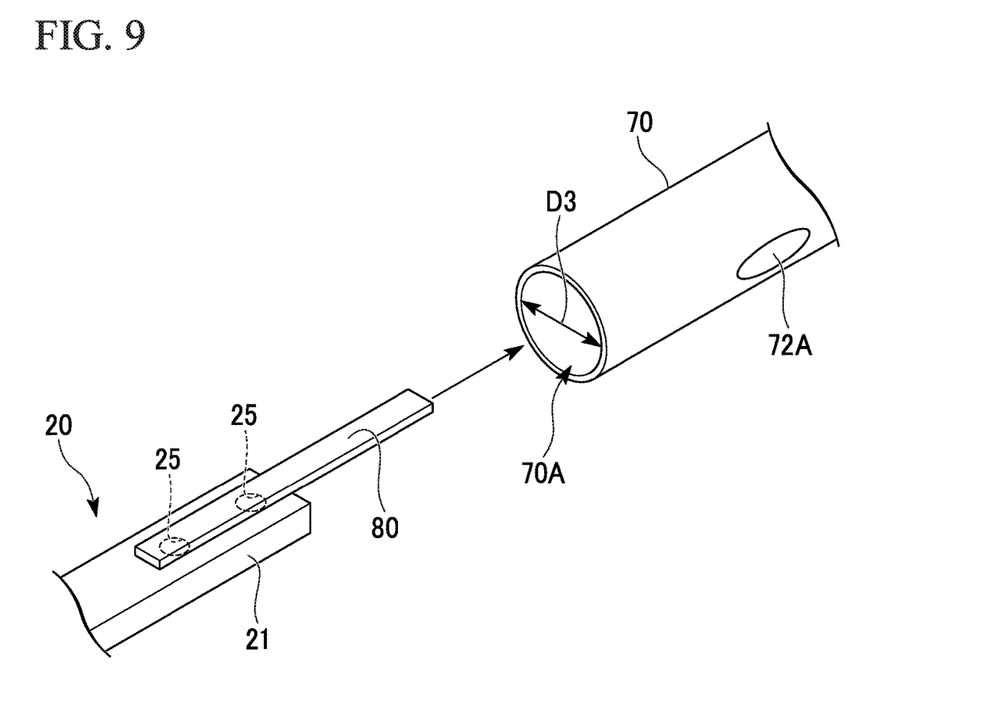
FIG. 9 is an explanatory diagram showing operation of drawing an imaging module into a tube forming the imaging-module-attached catheter according to one or more embodiments of the invention.

Next, an operation of drawing the imaging module 1 into the inside of the tube 70 of the catheter 60, that is, a manufacturing step of the catheter 60 will be described with reference to FIG. 9.

Firstly, the imaging module 1 having the first substrate 10 and the second substrate 20 which are connected to each other with the signal cable 30 interposed therebetween is prepared. Moreover, a jig 80 is prepared, the jig 80 is attached to the attachment holes 25 of the second substrate main body 21. In the example shown in FIG. 9, the jig 80 has a length such that the jig slightly extends from the end of the second substrate main body 21; however, the length of the jig 80 is not particularly limited. As a material used to form the jig 80, a material is adopted which has a higher degree of rigidity than that of a material the tube 70 and does not bend in the operation of drawing into the imaging module 1 into the inside of the tube 70.

Subsequently, the jig 80 is inserted into the module insertion opening 70A, furthermore, the jig 80 is inserted through the cable insertion opening 70B into the inside of the cable arrangement region 75, and the jig 80 moves toward the second substrate output port 76. Finally, the jig 80 is extracted from the second substrate output port 76.

In accordance with the above-described movement of the jig 80, the second substrate 20 is inserted into the module insertion opening 70A, the second substrate 20 is inserted through the cable insertion opening 70B into the inside of the cable arrangement region 75, the second substrate 20 moves toward the second substrate output port 76. Finally, the second substrate 20 is extracted from the second substrate output port 76.

In the movement of the second substrate 20 mentioned above, since the internal diameter D3 of the module insertion opening 70A is larger than or equal to the length D2 of the second diagonal line T2 on the outer end face 21E of the second substrate main body 21 (condition D3≥D2), there is no possibility that the second substrate 20 is caught by the module insertion opening 70A. In addition, since the internal diameter D4 of the cable insertion opening 70B (cable arrangement region 75) is larger than or equal to the length D2 (condition D4≥D2), there is no possibility that the second substrate 20 is caught by the cable insertion opening 70B.

In accordance with the above-described movement of the second substrate 20, the signal cable 30 connected to the second substrate 20 is disposed inside the cable arrangement region 75. Furthermore, the first substrate 10 and part of the signal cable 30 are disposed in the module arrangement region 71.

According to the above-mentioned movement of the second substrate 20 and the movements of the first substrate 10 and the signal cable 30, the solid-state image sensing device 40 comes into contact with the module insertion opening 70A. Here, since the internal diameter D3 of the module insertion opening 70A is less than or equal to the length D1 of the first diagonal line T1 on the light-receiving face 41 (condition D1≥D3), the solid-state image sensing device 40 is in a state of being attached to the module insertion opening 70A without being inserted into the inside of the tube 70.

According to one or more embodiments of the invention, it is possible to easily draw the imaging module 1 into the inside of the tube 70 of the catheter 60. Particularly, the second substrate 20 can be smoothly extracted from the second substrate output port 76 without being caught by the module insertion opening 70A and the cable insertion opening 70B. Also, it is possible to attach the solid-state image sensing device 40 to the module insertion opening 70A. Moreover, since an outer diameter of the catheter 60 does not increase, it is possible to achieve the catheter 60 that includes both the channel and the imaging module and has a small diameter.

In other cases, a wire or the like may be used as the jig 80 in one or more embodiments of the invention. In this case, a wire is prepared which has a length longer than the overall length of the tube 70, the wire is inserted into the inside of the cable arrangement region 75 so that the wire is exposed from the module insertion opening 70A and the second substrate output port 76. Thereafter, the end of the wire is attached to the attachment holes 25 shown in FIG. 9, and the wire exposed from the second substrate output port 76 is pulled to the outside. Accordingly, a tension occurs in the wire, the second substrate 20 is inserted into the module insertion opening 70A. Even in the case of using the above-described wire as the jig 80, the same effects as the in the aforementioned case is obtained.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. An imaging module comprising:
   an image-sensing device comprising an image-sensing device electrode;
   a first substrate comprising:
      a first insulating substrate main body;
      a first wiring disposed on the first insulating substrate main body;
      an electrode terminal electrically connected to the image-sensing device electrode and the first wiring; and
      a first cable terminal disposed on a surface of the first insulating substrate main body, and electrically connected to the first wiring;
   a second substrate comprising:
      a second insulating substrate main body;
      a second wiring disposed on the second insulating substrate main body; and a second cable terminal disposed on a surface of the second insulating substrate main body, and electrically connected to the second wiring; and a signal cable disposed between the first substrate and the second substrate and that electrically connects the first cable terminal to the second cable terminal, wherein D1 is a length of a first diagonal line on a light-receiving face of the image-sensing device, D2 is a length of a second diagonal line on an end face of the second insulating substrate main body, and D2 is less than or equal to D1.

2. The imaging module according to claim 1, wherein the signal cable is arranged inside a circumscribed circle of the second insulating substrate main body, and a diameter of the circumscribed circle corresponds to the length of the second diagonal line.

3. The imaging module according to claim 1, wherein the image-sensing device electrode is disposed on an electrode surface of the image-sensing device, and the first substrate is connected to the electrode surface so that an end face of the first insulating substrate main body is disposed between two of the image-sensing device electrode.

4. The imaging module according to claim 1, wherein the second substrate comprises:

a first surface;

a second surface opposite to the first surface; and a through electrode that penetrates through the second insulating substrate main body between the first surface and the second surface, and the second wiring is disposed on the first surface and second surface, and is electrically connected to the through electrode.

5. The imaging module according to claim 4, wherein the second substrate comprises an external connection terminal disposed on the second insulating substrate main body, and the external connection terminal is electrically connected to the second wiring.

6. The imaging module according to claim 5, wherein the external connection terminal is disposed on the first surface of the second substrate.

7. The imaging module according to claim 5, wherein the external connection terminal is disposed on the second surface of the second substrate.

8. The imaging module according to claim 1, wherein the signal cable is a coaxial cable.

9. An imaging-module-attached catheter comprising:

the imaging module according to claim 1; and a tube comprising:

a module arrangement region where the first substrate and a portion of the signal cable are arranged; and a channel disposed between the first cable terminal and the second cable terminal and next to the module arrangement region, wherein, in a view from the image-sensing device, the channel is disposed within an outline of the image-sensing device on a plane of projection.

* * * * *